(12) United States Patent
Nishioka

(10) Patent No.: US 7,053,397 B1
(45) Date of Patent: May 30, 2006

(54) FLUORESCENT IMAGE READING APPARATUS

(75) Inventor: Yukinori Nishioka, Kanagawa-ken (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 639 days.

(21) Appl. No.: 09/140,751

(22) Filed: Aug. 25, 1998

(30) Foreign Application Priority Data

Aug. 29, 1997 (JP) .......................................... 10-233747

(51) Int. Cl.
*G03B 42/08* (2006.01)

(52) U.S. Cl. ...................................................... 250/586

(58) Field of Classification Search ................. 250/586, 250/584, 580
See application file for complete search history.

(56) References Cited

U.S. PATENT DOCUMENTS

| | | | | |
|---|---|---|---|---|
| 4,825,246 A | * | 4/1989 | Fukuchi et al. ................. 355/4 |
| 4,926,045 A | * | 5/1990 | Hosoi et al. ............. 250/327.2 |
| 5,115,304 A | * | 5/1992 | Yoshikawa et al. ............ 358/75 |
| 5,300,767 A | * | 4/1994 | Steinle et al. ............ 250/208.1 |
| 5,325,217 A | * | 6/1994 | Nagler et al. ................ 358/506 |
| 5,414,489 A | * | 5/1995 | Kaplan ......................... 355/67 |
| 5,910,816 A | * | 6/1999 | Fontenot ....................... 348/65 |
| 5,998,802 A | * | 12/1999 | Struye et al. ................ 250/584 |
| 6,124,597 A | * | 9/2000 | Shehada et al. ......... 250/458.1 |

FOREIGN PATENT DOCUMENTS

| | | | | |
|---|---|---|---|---|
| JP | 2-306235 A | * | 12/1990 | ................. 250/586 |
| JP | 05-034847 A | | 2/1993 | |
| JP | 05-256763 A | | 10/1993 | |
| JP | 07-333234 A | | 12/1995 | |
| JP | 07-209510 A | | 8/1996 | |
| JP | 08-304284 A | | 11/1996 | |

* cited by examiner

*Primary Examiner*—Constantine Hannaher
(74) *Attorney, Agent, or Firm*—Sughrue Mion, PLLC

(57) ABSTRACT

A fluorescent image reading apparatus includes stimulating ray sources each adapted for emitting a stimulating ray toward an image carrier carrying a fluorescent image and causing it to release fluorescent light, a CCD and a filter disposed on the side of the CCD facing the image carrier, the filter including a color glass filter for cutting the stimulating ray and transmitting the fluorescent light and a dichroic coating for cutting the stimulating ray and transmitting the fluorescent light disposed on the side of the color glass filter facing the image carrier. According to the thus constituted fluorescent image reading apparatus, it is possible to improve the S/N ratio by cutting the stimulating ray and fluorescent light to prevent them from causing noise in image data.

10 Claims, 6 Drawing Sheets

FLUORESCENT IMAGE READING APPARATUS

BACKGROUND OF THE INVENTION

The present invention relates to a fluorescent image reading apparatus and, particularly, to such an apparatus which can improve the S/N ratio by cutting a stimulating ray and fluorescent light to prevent them from causing noise in the image data.

DESCRIPTION OF THE PRIOR ART

A fluorescence system using a fluorescent substance as a labeling substance is known. According to this system, it is possible to study a genetic sequence, the expression level of a gene and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed or distributing a plurality of DNA fragments on a gel support containing a fluorescent dye or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescent light, detecting the released fluorescent light to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescent light, detecting the released fluorescent light to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescent light releasing property, exciting the thus produced fluorescent substance by a stimulating ray to release fluorescent light, detecting the fluorescent light to produce an image and detecting the distribution of the target DNA on the transfer support. This fluorescence detecting system is advantageous in that a genetic sequence or the like can be easily detected without using a radioactive substance.

An image reading apparatus for such a fluorescence detecting system produces image data by irradiating a specimen carrying a fluorescent image with a stimulating ray from a light source to produce fluorescent light, converging the fluorescent light onto the surface of light receiving elements of a CCD camera by a lens, thereby photoelectrically detecting it and digitizing it. Since the S/N ratio becomes low if the CCD camera detects the stimulating ray, the image reading apparatus is provided in front of the lens with a color glass filter capable of cutting the stimulating ray so as to prevent the stimulating ray from impinging on the surface of the light receiving elements of the CCD camera.

However, when the color glass filter for cutting the stimulating ray is irradiated with the stimulating ray, it emits fluorescent light and this fluorescent light passes through the color glass filter to impinge on the surface of the light receiving elements of the CCD camera. Therefore, the S/N ratio cannot be sufficiently improved merely by providing the color glass filter for cutting the stimulating ray.

SUMMARY OF THE INVENTION

It is therefore an object of the present invention is to provide a fluorescent image reading apparatus which can improve the S/N ratio by cutting the stimulating ray and fluorescent light to prevent them from causing noise in image data.

The above and other objects of the present invention can be accomplished by a fluorescent image reading apparatus comprising at least one stimulating ray source for emitting a stimulating ray toward an image carrier carrying a fluorescent image and causing it to release fluorescent light, a CCD and a filter disposed on the side of the CCD facing the image carrier, the filter comprising a color glass filter for cutting the stimulating ray and transmitting the fluorescent light and a dichroic coating for cutting the stimulating ray and transmitting the fluorescent light disposed on the side of the color glass filter facing the image carrier.

In a preferred aspect of the present invention, the filter further comprises an infrared light-cut filter disposed on the side of the color glass filter facing the CCD.

The above and other objects and features of the present invention will become apparent from the following description made with reference to the accompanying drawings.

DESCRIPTION OF THE PREFERRED EMBODIMENT

Figure 1:
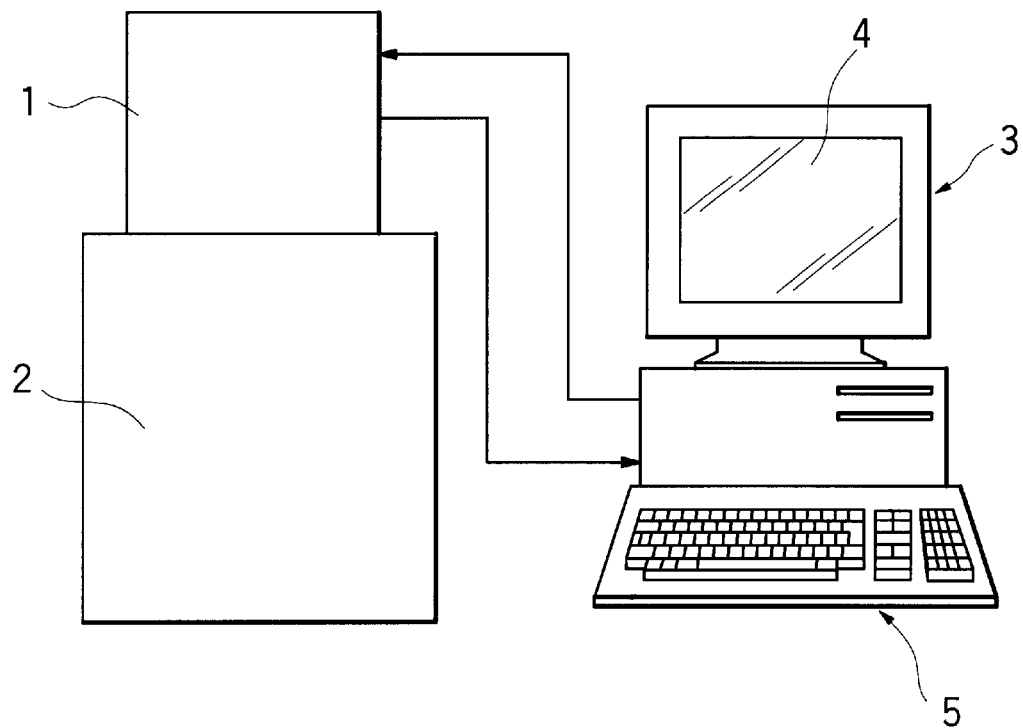
FIG. 1 is a schematic front view showing an image producing system including a fluorescent image reading apparatus which is a preferred embodiment of the present invention.

As shown in FIG. 1, an image producing system includes a cooled CCD camera 1, a dark box 2 and a personal computer 3. The personal computer 3 is equipped with a CRT 4 and a keyboard 5.

Figure 2:
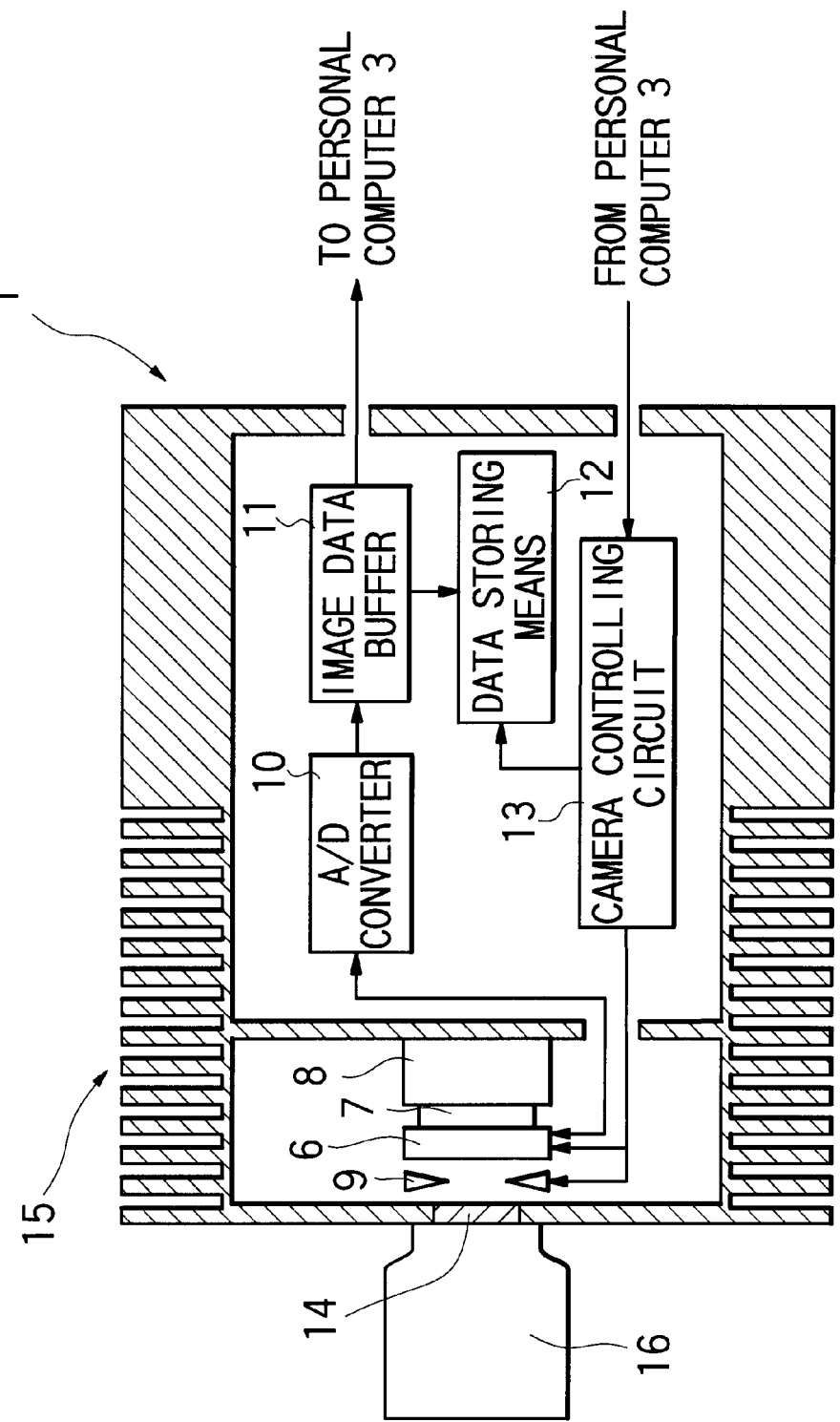
FIG. 2 is a schematic longitudinal cross sectional view showing a cooled CCD camera.

FIG. 2 is a schematic longitudinal cross sectional view showing the cooled CCD camera 1.

As shown in FIG. 2, the cooled CCD camera 1 includes a CCD 6, a heat transfer plate 7 made of metal such as aluminum, a Peltier element 8 for cooling the CCD 6, a shutter 9 disposed in front of the CCD 6, an A/D converter 10 for converting analog image data produced by the CCD to digital image data, an image data buffer 11 for temporarily storing an image digitized by the A/D converter 10, data storing means 12 for storing digital image data together with imaging conditions under which the image data was produced and a camera control circuit 13. An opening formed between the dark box 2 and the cooled CCD camera 1 is closed by a glass plate 14 and the periphery of the cooled CCD camera 1 is formed with heat dispersion fins 15 over substantially half its length for dispersing heat. The data storing means 12 is controlled by the camera control circuit 13 so as to be accessible.

A camera lens 16 disposed in the dark box 2 is mounted on the front surface of the glass plate 14 disposed in the cooled CCD camera 1.

Figure 3:
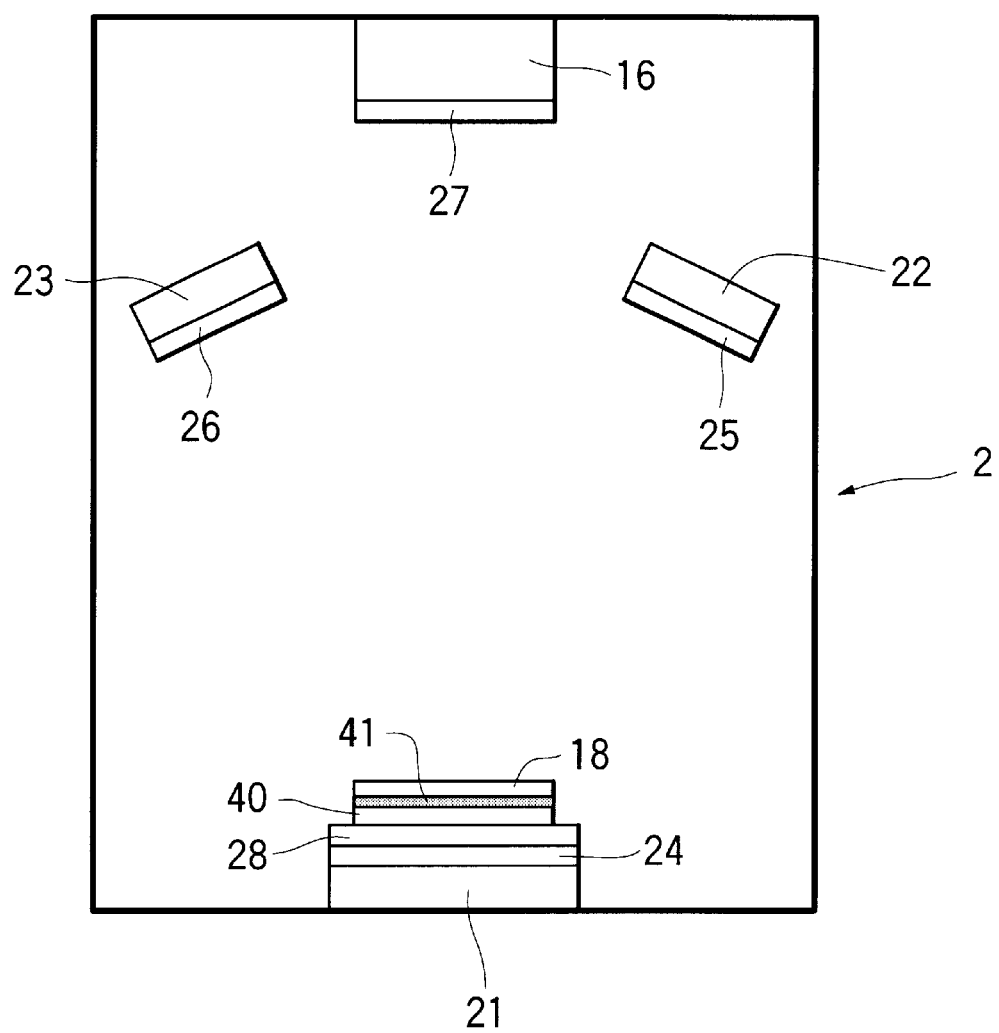
FIG. 3 is a schematic vertical cross sectional view showing a dark box.

FIG. 3 is a schematic vertical cross sectional view showing a dark box 2.

As shown in FIG. 3, the dark box 2 is equipped with a first blue light emitting diode stimulating ray source 21 for emitting a stimulating ray whose center wavelength is 450 nm, and a second blue light emitting diode stimulating ray source 22 and a third blue light emitting diode stimulating ray source 23 are provided obliquely above the first blue light emitting diode stimulating ray source 21, each being adapted for emitting a stimulating ray whose center wavelength is 450 nm. A filter 24 is adhered to the upper surface of the first blue light emitting diode stimulating ray source 21 and filters 25, 26 are respectively adhered to the front surfaces of the second blue light emitting diode stimulating ray source 22 and the third blue light emitting diode stimulating ray source 23. The filters 24, 25, 26 cut light of wavelengths other than one in the vicinity of 450 nm and harmful to the stimulation of a fluorescent substance and transmit light having a wavelength in the vicinity of 450 nm. A filter 27 for cutting the stimulating ray having a wavelength in the vicinity of 450 nm is detachably provided on the front surface of the camera lens 16. A diffusion plate 28 is mounted on the upper surface of the filter 24 for diffusing the stimulating ray emitted from the first blue light emitting diode stimulating ray source 21. A sample stage 40 is placed on the upper surface of the diffusion plate 28 and a diffusion plate 41 is mounted on the upper surface of the sample stage 40 for diffusing the stimulating ray emitted from the first blue light emitting diode stimulating ray source 21 so as to uniformly project onto an image carrier 18 to be placed thereon. In this embodiment, opposite side walls of the dark box 2 are formed with shelves (not shown) adapted for fixing the sample stage 40 on which an image carrier 18 carrying a fluorescent image is to be placed, thereby enabling the vertical position of the sample stage 40 to be varied over seven steps.

Figure 4:
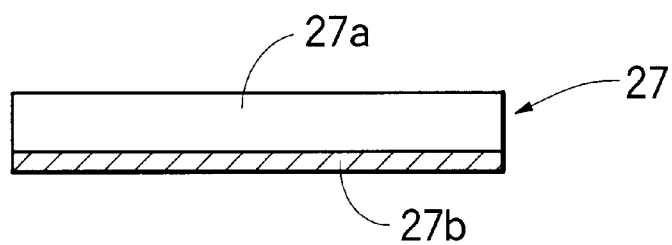
FIG. 4 is a schematic cross sectional view showing a filter.

FIG. 4 is a schematic cross sectional view showing the filter 27.

Figure 5:
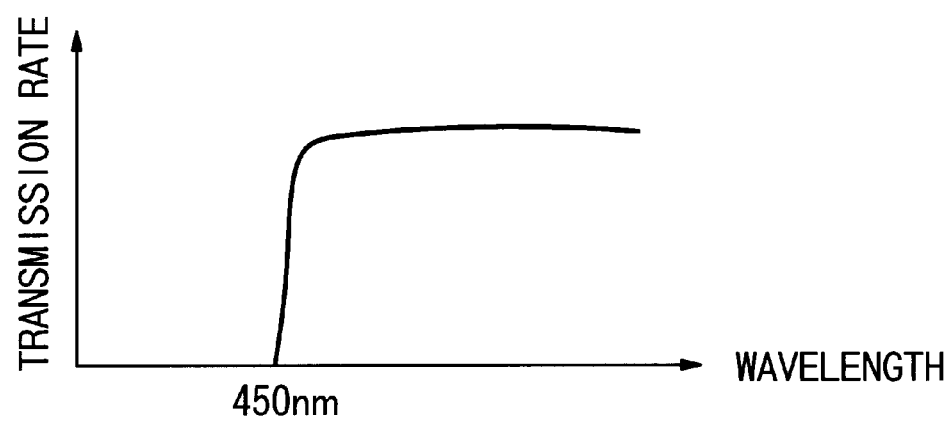
FIG. 5 is a diagram showing transmission properties of a color glass filter and a dichroic coating.

As shown in FIG. 4, the filter 27 includes a color glass filter 27a and a dichroic coating 27b formed on the surface of the color glass filter 27a on the side of the sample stage 40. The color glass filter 27a and the dichroic coating 27b have the transmission properties shown in FIG. 5 so as to cut light having a wavelength in the vicinity of 450 nm and transmit light having a wavelength longer than 450 nm. Since the wavelength of fluorescent light caused by the stimulation of a fluorescent substance is longer than the wavelength of the stimulating ray, the dichroic coating 27b cuts the stimulating ray having a wavelength in the vicinity of 450 nm but can transmit fluorescent light emitted from the fluorescent substance upon being stimulated. Since the dichroic coating 27b, which cuts light having a wavelength in the vicinity of 450 nm and transmits fluorescent light emitted from the fluorescent substance, is formed on the surface of the color glass filter 27a on the side of the sample stage 40, when a stimulating ray emitted from the first blue light emitting diode stimulating ray source 21, the second blue light emitting diode stimulating ray source 22 or the third blue light emitting diode stimulating ray source 23 enters the filter 27, most of the stimulating ray is cut by the dichroic coating 27b and only a very small amount of the stimulating ray impinges on the color glass filter 27a. Therefore, it is possible to effectively prevent fluorescent light produced by the color glass filter 27a upon excitation by the stimulating ray from impinging on the light receiving surface of the CCD 6 and being detected and thus to prevent noise from being generated in the image data.

Figure 6:
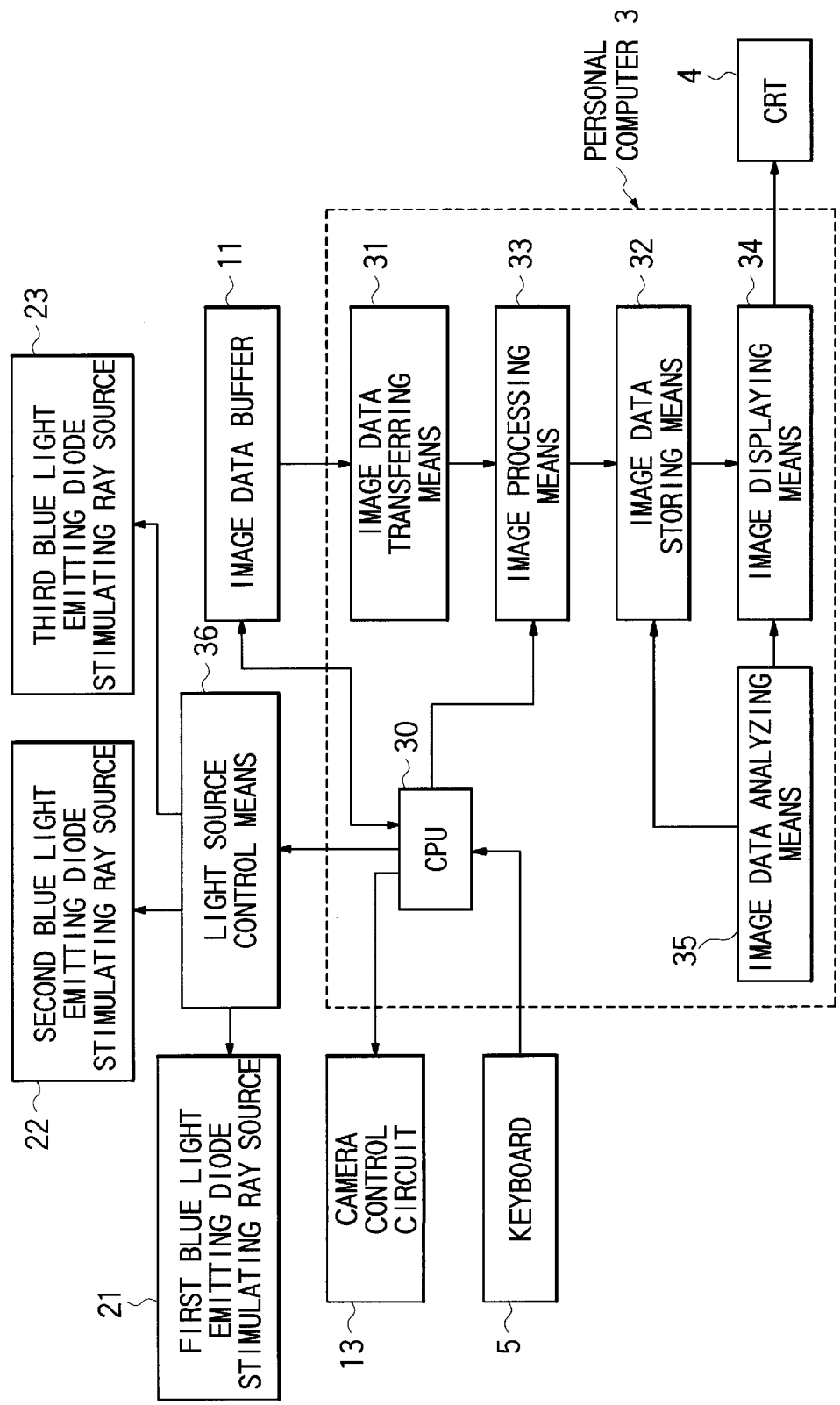
FIG. 6 is a block diagram of a personal computer and peripheral devices thereof.

FIG. 6 is a block diagram of the personal computer 3 and peripheral devices thereof.

As shown in FIG. 6, the personal computer 3 includes a CPU 30 for controlling the exposure of the cooled CCD camera 1, an image data transferring means 31 for reading the image data produced by the cooled CCD camera 1 from the image data buffer 11, an image processing means 33 for effecting image processing on the image data read out by the image transferring means 31 and storing them in an image data storing means 32, an image displaying means 34 for displaying a visual image on the screen of the CRT 4 based on the image data stored in the image data storing means 32, and an image data analyzing means 35 for analyzing the image data stored in the image data storing means 32. The first blue light emitting diode stimulating ray source 21, the second blue light emitting diode stimulating ray source 22 and the third blue light emitting diode stimulating ray source 23 are controlled by a light source control means 36 and an instruction signal can be input via the CPU 30 to the light source control means 36 through the keyboard 5. The CPU 30 is constituted so as to output various signals to the camera controlling circuit 13 of the cooled CCD camera 1. The image data storing means 32 is constituted so as to store image data together with imaging conditions under which the image data was produced and is accessible by the CPU 30.

The fluorescent image reading apparatus according to this embodiment is constituted so that an image carrier 18 carrying an image of a fluorescent substance is irradiated with a stimulating ray from the first blue light emitting diode stimulating ray source 21 alone or the second blue light emitting diode stimulating ray source 22 and the third blue light emitting diode stimulating ray source 23 and fluorescent light emitted from the image carrier 18 is detected through the camera lens 16 by the CCD 6 of the cooled CCD camera 1, thereby producing a fluorescent image. As termed in this specification, an image carrier carrying an image of a fluorescent substance includes an image carrier carrying an image of a specimen labeled with a fluorescent substance and an image carrier carrying an image of a fluorescent substance obtained by combining enzyme with a labeled specimen, contacting the enzyme and a fluorescent substrate, thereby changing the fluorescent substrate to a fluorescent substance capable of emitting fluorescent light.

The thus constituted fluorescent image reading apparatus which is an embodiment of the present invention produces a fluorescent image using the first blue light emitting diode stimulating ray source 21.

An image carrier 18 is first placed on the diffusing plate 41 formed on the sample stage 40 and the lens focus is adjusted by the user. After the dark box 2 has been closed, the user inputs an exposure start signal through the keyboard 5. The first blue light emitting diode stimulating ray source 21 is turned on by the light source control means 36, thereby emitting a stimulating ray toward the image carrier 18 placed on the diffusion plate 41. At the same time, the exposure start signal is input through the CPU 30 to the camera controlling circuit 13 of the cooled CCD camera 1 and the shutter 9 is opened by the camera controlling circuit 13, thereby starting the exposure of the CCD 6.

Light components of wavelengths not in the vicinity of 450 nm are cut by the filter 27 from the stimulating ray emitted from the first blue light emitting diode stimulating ray source 21. As a result, the fluorescent substance contained in the image carrier 18 is stimulated by light having a wavelength in the vicinity of 450 nm, thereby emitting fluorescent light.

The fluorescent light emitted from the fluorescent substance contained in the image carrier 18 impinges on the light receiving surface of a light receiving sensor 60 of the CCD 6 through the filter 27 and the camera lens 16 and forms an image thereon. The light receiving sensor 60 of the CCD 6 receives light of the thus formed image and accumulates it in the form of electric charges therein. In this embodiment, in the case where the stimulating ray emitted from the first blue light emitting diode stimulating ray source 21 enters the filter 27, most of the stimulating ray having a wavelength in the vicinity of 450 nm is cut by the dichroic coating 27b formed on the surface of the color glass filter 27a on the side of the sample stage 40 and only a very small amount of the stimulating ray impinges on the color glass filter 27a. Therefore, it is possible to effectively prevent the stimulating ray from impinging on the color glass filter 27a and exciting the color glass filter 27a to produce fluorescent light. As a result, fluorescent light caused by stimulation of the color glass filter 27a with the stimulating ray is prevented from impinging on the light receiving surface of the light receiving sensor 60 of the CCD 6 and noise is prevented from being generated in the image data. Thus, only fluorescent light emitted from the fluorescent substance contained in the image carrier 18 is received by the CCD 6.

When a predetermined exposure time has passed, the CPU 30 outputs an exposure completion signal to the camera controlling circuit 13 of the cooled CCD camera 1. When the camera controlling circuit 13 receives the exposure completion signal from the CPU 30, it transfers the analog image data accumulated in the CCD 6 in the form of electric charge to the A/D converter 10 to cause the A/D converter 10 to digitize the image data and temporarily store the thus digitized image data in the image data buffer 11 together with the imaging conditions. The image data and the imaging conditions under which the image data was produced temporarily stored in the image data buffer 11 are input to the data storing means 12 and stored therein. At the same time, the CPU 30 outputs a data transfer signal to the image data transferring means 31 to cause it to read out the digital image data temporarily stored in the image data buffer 11 of the cooled CCD camera 1 together with the imaging conditions and to input them to the image processing means 33.

The image processing means 33 effects predetermined image processing on the image data input from the image data transferring means 31 and stores them in the image data storing means 32.

Afterward, when the user inputs an image production signal through the keyboard 5, the image displaying means 34 reads out the image data stored in the image data storing means 32 and a fluorescent image is displayed on the screen of the CRT 4 based on the read out image data.

On the other hand, when the user inputs an analyzing signal through the keyboard 5, the image data analyzing means 35 reads out image data and the imaging conditions under which the image data was produced stored in the image data storing means 32 and analyzes the image data specified by the user and the result of the analysis is displayed on the screen of the CRT 4 by the image displaying means 34.

According to the above described embodiment, the filter 27 detachably mounted on the front surface of the camera lens 16 includes the color glass filter 27a and the dichroic coating 27b formed on the surface of the color glass filter 27a on the side of the sample stage 40. The the dichroic coating 27b on the surface of the color glass filter 27a on the side of the sample stage 40 is adapted to cut light having a wavelength in the vicinity of 450 nm and transmit fluorescent light emitted from a fluorescent substance. Therefore, in the case where a stimulating ray emitted from the first blue light emitting diode stimulating ray source 21, the second blue light emitting diode stimulating ray source 22 or the third blue light emitting diode stimulating ray source 23 enters the filter 27, most of the stimulating ray is cut by the dichroic coating 27b and only a very small amount of the stimulating ray impinges on the color glass filter 27a. As a result, it is possible to effectively prevent fluorescent light produced by the color glass filter 27a upon excitation by the stimulating ray from impinging on the light receiving surface of the CCD 6 and being detected and thus to prevent noise from being generated in the image data.

Figure 7:
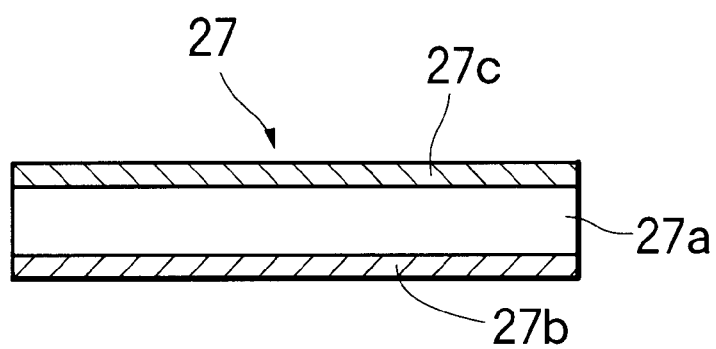
FIG. 7 is a schematic cross sectional view showing another configuration of a filter.

FIG. 7 is a schematic cross sectional view showing another configuration of the filter 27 detachably mounted on the front surface of the camera lens 16.

As shown in FIG. 7, the filter 27 includes a color glass filter 27a, a dichroic coating 27b formed on the surface of the color glass filter 27a on the side of the sample stage 40 and an infrared light-cut filter 27c adhered to the surface of the color glass filter 27b on the side of the camera lens 16. Therefore, in a fluorescent image reading apparatus in which the filter 27 shown in FIG. 7 is mounted on the front surface of the camera lens 16 and which is another embodiment of the present invention, not only is the stimulating ray cut but infrared light detectable by the CCD 6 is also cut by the infrared light-cut filter 27c of the filter 27. It is therefore possible to to markedly improve the S/N ratio by preventing infrared light from impinging on the light receiving surface of the light receiving sensor 60 of the CCD 6 and being detected to cause noise in the image data.

The present invention has thus been shown and described with reference to specific embodiments. However, it should be noted that the present invention is in no way limited to the details of the described arrangements but changes and modifications may be made without departing from the scope of the appended claims.

For example, although the cooled CCD camera 1 is used in the above described embodiments, a CCD camera having no cooling means can be used for producing image data in cases where, unlike fluorescent imaging, it is unnecessary to detect weak light.

Further, although in the above described embodiments, the first blue light emitting diode stimulating ray source 21, the second blue light emitting diode stimulating ray source 22 and the third blue light emitting diode stimulating ray source 23 are provided in the dark box 2, only the first blue light emitting diode stimulating ray source 21 or only the second blue light emitting diode stimulating ray source 22 and the third blue light emitting diode stimulating ray source 23 may be provided therein.

Moreover, although in the above described embodiments, the blue light emitting diode stimulating ray sources 21, 22, 23 for emitting stimulating rays with a center wavelength of 450 nm are used, light emitting diode stimulating ray sources for emitting stimulating rays with a center wavelength in the range between 400 nm and 700 nm may be employed depending on the kind of fluorescent substance.

Further, although in the above described embodiments, the cooled CCD camera 1 is formed with heat dispersion fins 15 over substantially half its length for dispersing heat released from the Peltier element 8, it is possible to form the heat dispersion fins 15 on the periphery of the cooled CCD camera 1 over its entire length and the arrangement of the heat dispersion fins 15 on the periphery of the cooled CCD camera 1 may be arbitrarily determined.

Furthermore, in the above described embodiments, the second blue light emitting diode stimulating ray source 22 and the third blue light emitting diode stimulating ray source 23 are used as downward flooding type light sources. However, the number of the downward flooding type stimulating ray sources is not limited to two and it is possible to provide three or more, for example four, downward flooding type stimulating ray sources.

Further, in the present invention, the respective means need not necessarily be physical means and arrangements whereby the functions of the respective means are accomplished by software fall within the scope of the present invention. In addition, the function of a single means may be accomplished by two or more physical means and the functions of two or more means may be accomplished by a single physical means.

According to the present invention, it is possible to provide a fluorescent image reading apparatus which can improve the S/N ratio by cutting the stimulating ray and fluorescent light to prevent them from causing noise in image data.

What is claimed is:

1. A fluorescent image reading apparatus comprising at least one stimulating ray source for emitting a stimulating ray toward an image carrier carrying a fluorescent image and causing said image carrier to release fluorescent light, a CCD and a filter disposed on the side of the CCD facing the image carrier, the filter comprising a color glass filter for cutting the stimulating ray and transmitting the fluorescent light and a dichroic coating for cutting the stimulating ray and transmitting the fluorescent light disposed on the side of the color glass filter facing the image carrier, wherein said dichroic coating cuts off light at and below a predetermined wavelength and transmits light above the predetermined wavelength and said filter further comprises an infrared light cut-off filter disposed on the side of the color glass filter facing the CCD.

2. The fluorescent image reading apparatus of claim 1 wherein said predetermined wavelength is within a range of 400–700 nm.

3. The fluorescent image reading apparatus of claim 1 wherein said glass filter has cut off characteristics similar to said dichroic coating.

4. The fluorescent image reading apparatus of claim 1, wherein said dichroic coating cuts off light having a wavelength of approximately 450 nm.

5. A fluorescent image reading apparatus comprising:
    at least one stimulating ray source for emitting a stimulating ray toward an image carrier carrying a fluorescent image and causing said image carrier to release fluorescent light;
    a CCD detecting the fluorescent light;
    a filter disposed on the CCD facing the image carrier, said filter spaced from the image carrier by free space and having no physical elements intervening between opposing surfaces of the image carrier and the filter, and wherein the filter comprises a color glass filter for cutting stimulating rays and transmitting the fluorescent light and a dichroic coating for cutting the stimulating ray and transmitting the fluorescent light disposed on the side of the color glass filter facing the image carrier, and wherein said dichroic coating cuts off light at and below a predetermined wavelength and transmits light above the predetermined wavelength.

6. The fluorescent image reading apparatus according to claim 5, wherein the opposing surfaces of the filter and the image carrier are essentially parallel to teach other.

7. The fluorescent image reading apparatus according to claim 6, wherein the filter and CCD are in direct physical connection with each other.

8. The fluorescent image reading apparatus according to claim 7, wherein filter further comprises an infrared filter facing the CCD, wherein the CCD and the infrared filter are in direct physical connection with each other.

9. The fluorescent image reading apparatus according to claim 8, wherein the filter and image carrier are disposed in a housing which is opaque to light.

10. The fluorescent image reading apparatus according to claim 9, further comprising a second stimulating ray source disposed in the housing, wherein said at least one stimulating ray source and said second stimulating ray source are disposed on opposite sides of the image carrier.

* * * * *

UNITED STATES PATENT AND TRADEMARK OFFICE
CERTIFICATE OF CORRECTION

PATENT NO.       : 7,053,397 B1                                    Page 1 of 1
APPLICATION NO.  : 09/140751
DATED            : May 30, 2006
INVENTOR(S)      : Yukinori Nishioka It is certified that error appears in the above-identified patent and that said Letters Patent is hereby corrected as shown below:

Title Page, Item (30) Foreign Application Priority Data should read Aug. 29, 1997, (JP) .................09-233747

Signed and Sealed this

Thirtieth Day of January, 2007

JON W. DUDAS
*Director of the United States Patent and Trademark Office*